United States Patent [19]

Okada

[11] Patent Number: 4,794,911

[45] Date of Patent: Jan. 3, 1989

[54] MEANS TO FACILITATE DETACHABLY MOUNTING CAP TO DISTAL END OF ENDOSCOPE

[75] Inventor: Minoru Okada, Hachioji, Japan

[73] Assignee: Olympus Optical Company Ltd., Japan

[21] Appl. No.: 85,512

[22] Filed: Aug. 13, 1987

[30] Foreign Application Priority Data

Sep. 20, 1986 [JP] Japan .............................. 61-144834[U]
Nov. 29, 1986 [JP] Japan .............................. 61-184462[U]

[51] Int. Cl.$^4$ ................................................ A61B 1/00
[52] U.S. Cl. ........................................... 128/4; 128/6
[58] Field of Search ....................... 128/3, 4, 5, 6, 7, 8; 350/96.26; 356/241

[56] References Cited

U.S. PATENT DOCUMENTS 4,329,980  5/1982  Terada ..................................... 128/4
4,706,653 11/1987  Yamamoto .............................. 128/4

Primary Examiner—William H. Grieb
Attorney, Agent, or Firm—Ostrolenk, Faber, Gerb & Soffen

[57] ABSTRACT

An endoscope includes a cap screw body rotatably mounted on a distal end member thereof and having a male threading means for mounting a cap, the cap detachably fitted on the distal end member and having a female threading means for threadably engaging with the cap screw body and a pin projectingly provided therein, and a fitting groove including an axial groove and a peripheral groove provided on the outer peripheral surface of the distal end member for fitting the pin, such that the cap is securely mounted by smoothly moving the pin along the fitting groove without binding between the male and female threading means while the pin moves within the peripheral groove.

8 Claims, 4 Drawing Sheets

FIG. IA
(PRIOR ART)
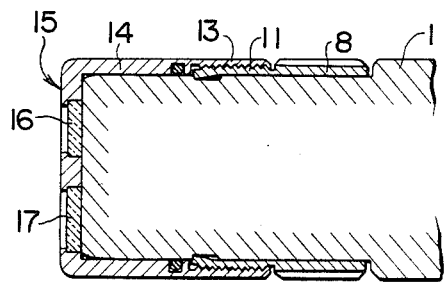
FIG. IB
(PRIOR ART)
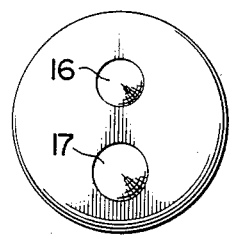
FIG. 2
(PRIOR ART)
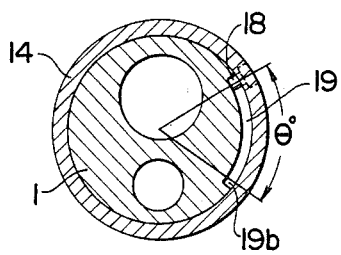
FIG. 3
(PRIOR ART)
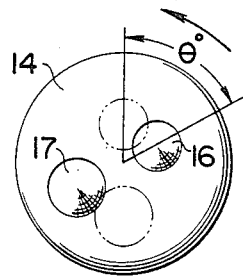

MEANS TO FACILITATE DETACHABLY MOUNTING CAP TO DISTAL END OF ENDOSCOPE

BACKGROUND OF THE INVENTION

The present invention relates to an endoscope, and more particularly, to a mounting structure of a cap which is detachably mounted on a distal end member of an insertable portion of an endoscope.

In an endoscope of the type having a structure in which a cap is mounted on the distal end of the insertable portion thereof, when the endoscope is inserted into a coelom with the cap mounted, it is necessary to completely prevent tee cap from falling off.

In the past, a cap has been mounted by fitting in a fitting groove formed on the outer periphery of a distal end member of an endoscope, or a cap having a female thread on its inner peripheral surface has been mounted by mating with a male thread formed on the outer peripheral surface of the distal end member.

With such a mounting structure, however, when the cap becomes loose while observing and operating with the insertable portion of the endoscope inserted into a coelom of a patient, there is a possibility that the cap may fall off in the coelom during an operation without being noticed by an operator that the cap has loosened.

Accordingly, the applicant, to overcome the disadvantages described above, has proposed an endoscope in Japanese Utility Model Publication Sho 61/1986-21043, in which a pin is provided on the inner peripheral surface of a cap and a fitting groove is provided on the outer peripheral surface of a distal end member of the endoscope such that the cap is rotated and drawn in the distal end member while the pin is fitted therein Such an endoscope will be described hereinafter with reference to FIGS. 1A and 1B to 4.

In FIG. 1A which is a diagram of the distal end of an endoscope with its inner structure omitted, a cap screw body 8 is rotatably fitted on the outer periphery of the distal end 1 of the endoscope so as not to fall off therefrom by limiting its axial position A male thread 11 is provided on the front outer peripheral surface of the cap screw body 8 such that a cap 14 is mounted on the distal end member 1 by threadably engaging a female thread 13 provided on the rear inner peripheral surface of the cap 14 with the male thread 11. An observation window 16 and an illumination window 17 are arranged on the distal end surface 15 of the cap 14 as shown in FIG. 1B. A pin 18 is provided on the inner peripheral surface of the cap 14 so as to project inwardly thereof (FIG. 2). The pin 18 is fitted into a peripheral groove 19b which is a strucuural element of a fitting groove 19 formed on the distal outer peripheral surface of the distal end member 1. The fitting groove 19 is formed in a crank-shaped configuration including axial grooves 19a and 19c and a peripheral groove 19b as shown in FIG. 4.

To mount the cap 14 on the distal end member 1, after the cap 14 is fitted on the distal end member 1 along the axial groove 19a thereof, the cap screw body 8 is rotated. Then, the cap 14 having the female thread 13 which engages the male thread 11 is fixed in place with rectilinear and rotational movements along the fitting groove 19 such that the observation and the illumination windows 16, 17 face the observation and illumination optical systems, respectively.

Accordingly, even if the cap 14 thus mounted loosens during observation, there is no possibility that the cap 14 falls off from the distal end member since the pin 18 stops on the front end side of the axial groove 19c. In addition, when the cap 14 loosens and the pin 18 moves to a position shown in FIG. 4, the observation and the illumination windows 16, 17 are shifted to positions shown in FIG. 3 by solid lines to reduce brightness, making an observed image dark and defective, so that an operator can discover that the cap 14 is loose.

In the disclosure of the Japanese Utility Model Publication described above, while the pin 18 moves along the fitting groove 19, the cap 14 is always in threadable engagement with the cap screw body 8. While the pin 18 moves along the axial grooves 19a and 19c, as shown in FIG. 4, only the cap screw body 8 is rotated, so that there is no problem. While the pin 18 moves along the peripheral groove 19b, however, only the cap 14 is rotated. At this time, since the cap screw body 8 is not moved and only the cap 14 is rotated, the pin 18 moves along an angle of inclination $\alpha_0$ of the male thread 11 (a lead angle) (see FIG. 4), so that the pin 18 may be pushed against the side wall of the peripheral groove 19b by the threading action to be brought into contact therewith and to cause binding between the male thread 11 and the female thread 13. Thus, there are problems that the cap 14 may not be removed or set up.

SUMMARY OF THE INVENTION

It is an object of the present invention to overcome the disadvantages described above in the prior art by providing an endoscope including a cap screw body rotatably mounted on a distal end member of the endoscope and having male threading means for mounting a cap, the cap detachably fitted into said distal end member and having female threading means for threadably engaging said cap screw body and a pin which is projectingly provided on the interior of the cap, and a fitting groove into which the pin is fitted and which comprises an axial groove and a peripheral groove which are provided on the peripheral surface of the distal end member, such that the cap can be easily mounted on the distal end member without causing binding or the like between threads of the male and female threading means by allowing the pin to smoothly move along the lock groove.

According to the present invention, while the pin of the cap moves in the peripheral groove, the male and female threading means for the cap and the cap screw body are released, so that the following remarkable effects can be obtained.

(i) Since binding between threads may not be caused while the pin moves in the peripheral groove, there is no problem that the cap may not be removed or set up.

(ii) Since for removing the cap it is required to once disengage and to again engage the thread of the screwing means, a reliability for preventing the cap from falling off during inspection increases.

Further, according to the present invention, since the peripheral groove of the fitting groove provided on the distal end member has an inclination of the same angle as the lead angle of the threading means of the cap screw body which engages the cap, when only the cap is allowed to rotate without moving the cap screw body, the pin moves in the peripheral groove having an inclination of the same angle as the lead angle of the threading means so that no binding may be caused between the threads.

BRIEF DESCRIPTION OF THE DRAWINGS

FIGS. 1A and B are section and front views showing essential parts of the distal end of a conventional endoscope, respectively;

FIG. 2 is a section view of a cap of a conventional endoscope;

FIG. 3 is a front view showing a rotational direction of the cap shown in FIG. 2;

DETAILED DESCRIPTION OF THE PREFERRED EMBODIMENTS

Figure 4:
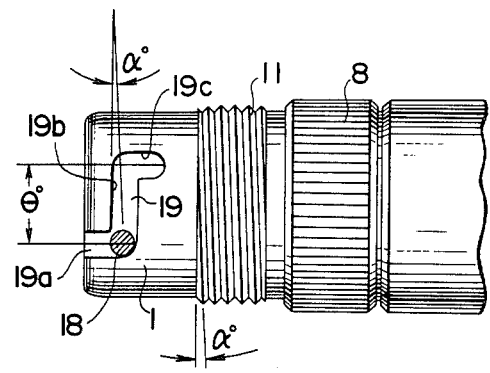
FIG. 4 is a side view showing movement of a pin when the cap shown in FIG. 2 is mounted on the endoscope.
Figure 5:
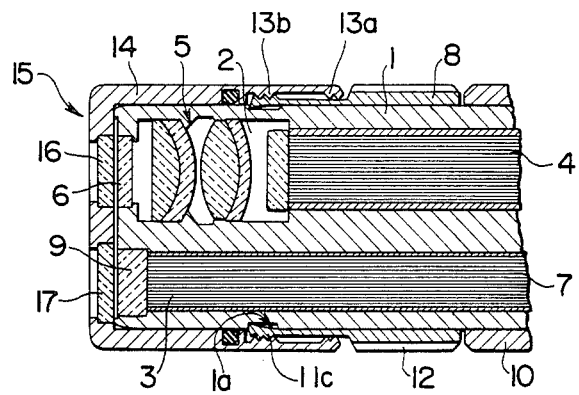
FIG. 5 is a section view of essential parts of the distal end of an endoscope according to a first embodiment of the present invention.
Figure 6:
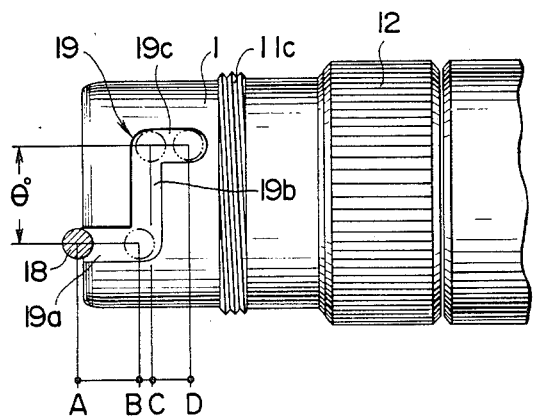
FIG. 6 is a side view of essential parts of the distal end of the endoscope shown in FIG. 5 from which a cap is removed.

FIGS. 5 and 6 show a first embodiment of the present invention, in which like reference characters denote similar parts to those in the prior art endoscope shown in FIGS. 1 to 8 and their description will be omitted.

In FIGS. 5 and 6, an observation optical system 2 and an illumination optical system 3 are arranged within a distal end member 1 made of a distal metal barrel of an endoscope. The observation optical system 2 comprises an image guide 4 formed of optical fiber bundles and inserted from the rear side of the endoscope, an objective lens optical system 5 disposed in front of the image guide 4 and a cover glass 6 disposed in front of the objective lens optical system 5. The illumination optical system 3 is constructed such that a light guide 7 formed of optical fiber bundles and disposed in parallel relationship with the image guide 4 is inserted into the endoscope until it abuts against a cover glass 9 disposed at the distal end thereof. A cap screw body 8 rotatably fitted on the outer periphery of the distal end member 1 has its front end abutting against one side wall of a peripheral groove 1a provided on the distal end member 1 and its rear end abutting against a structural member 10 of the distal end member 1 so that its movement in the axial direction is restricted. The cap screw body 8 is formed with a male thread 11c on its outer periphery towards its distal end and with a knurl 12 on its outer periphery in its rear half portion.

A cap 14 inside which two female threads 13a and 13b are provided in spacedly divided before and behind in the axial direction is fitted into the distal end of the distal end member 1 to be threadably secured to the cap screw body 8. On the front end surface 15 of the cap 14, an observation window 16 and an illumination window 17 are arranged so as to be in abutment with the cover glass 6 of the observation optical system 2 and the cover glass 9 of the illumination optical system 3 in alignment manner, respectively, when the cap 14 is mounted in place. In addition, a pin 18 is projectingly provided on the inner peripheral surface of the cap 14 as in the prior art endoscope. A fitting groove 19 is provided on the outer periphery of the distal end member 1, into which the pin 8 is fitted. The fitting groove 19 is formed in a crank-shaped configuration including axial grooves 19a and 19c and a peripheral groove 19b as in the prior art endoscope. The pin 18 has a height sufficient to be accommodated within the fitting groove 19.

When the cap 14 and the cap screw body 8 are mated with each other in place, the pin 18 is positioned at the terminal end of the axial groove 19c and the observation and illumination windows 16, 17 are in agreement with the cover glasses 6, 9, respectively.

In operation, the cap 14 is inserted into the distal end member 1 so that the pin 18 is fitted into the fitting groove 19. At this time, the pin 18 is at a position A in FIG. 6. Subsequently, the cap screw body 8 is rotated in such a manner that the female threads 13a of the cap 14 is threadably engaged with the male thread 11c of the cap screw body 8. With this rotation, the cap 14 is drawn in while the pin 18 moves along the axial groove 19a and the pin 18 reaches a position B adjacent to the rear end of the axial groove 19a. At this time, the male thread 11c and the female thread 13a are disengaged. At the position B, however, part of the pin 18 is still in contact with the side wall of the axial groove 19a, so that the pin 18 cannot be rotated in the peripheral direction at the position B. As described above, however, since the engagement between the distal end member 1 and the cap 14 has been already released, when the cap 14 or the pin 8 is slightly pushed in and is rotated counterclockwise viewing from the front side, the pin 8 rotates through an angle $\theta°$ along the peripheral groove 19b and stops striking against the side wall of the axial groove 19c. Thereupon, when the cap 14 or the pin 18 is further pushed in slightly, the male thread 11c is now mated with the other female thread 13b at a position C an the cap 14 or the pin 18 is drawn in along the axial groove 19c with rotation of the cap screw body 8. Then, the inner bottom surface of the cap 14 abuts against the front end surface of the distal end member 1 at a position D to complete the mounting operation of the cap 14. It will be understood that when the cap 14 is removed, the foregoing operations are reversed.

Figure 7A:
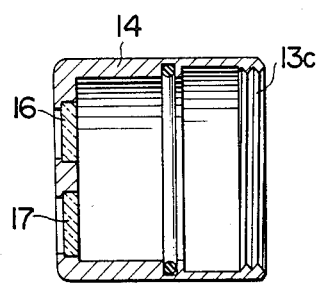
FIGS. 7A and B are a longitudinal sectional view of a cap and a side view of a distal end member of an endoscope according to a second embodiment of the present invention, respectively.

In FIGS. 7A and B, which show a second embodiment of the present invention, two male threads 11a, 11b spacedly divided in the axial direction are provided on the outer periphery of a cap screw body 8 and a female thread of a cap 14 to be mated with the male threads 11a, 11b are provided at the rear end of the cap 14 as a single female thread 13c. With this structure, when the cap 14 is fitted into the distal end member 1, the male thread 11a of the cap screw body 8 mates with the female thread 13c of the cap 14 while the pin 18 moves within the axial groove 19a. In addition, while the pin 18 moves within the axial groove 19c, the male thread 11b mates with the female thread 13c. While the pin 18 moves within the peripheral groove 19b, the cap 14 is disengaged to be free. Accordingly, operations are similar to those of the first embodiment and the same effects can be obtained.

In the present invention, it may be possible to construct the endoscope such that after the cap 14 is secured the knurl 12 of the cap screw body 8 is covered by a cover body connected to the cap. In addition, it may be possible to omit the knurl 12.

Figure 7B:
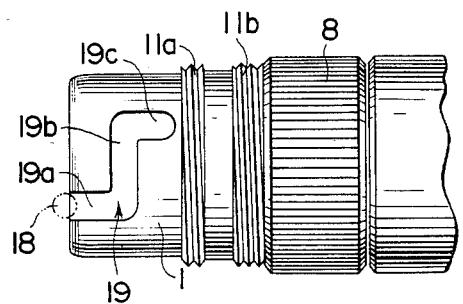

In the foregoing embodiment (FIGS. 5 and 6), the threading means includes one male thread provided on the cap screw body and two female threads provided on the cap at a slightly wider interval than the length of the male thread in its axial direction and the threading means of FIGS. 7A and 7B includes one female thread provided on the cap and two male threads provided on the cap screw body at a slightly wider interval than the length of the female thread in its axial direction. However, the threading means are not limited to these embodiments and it will be understood, in effect, that the thread engaging action between the cap and the cap screw body is released while the pin 18 moves within the peripheral groove 19b.

Figure 8:
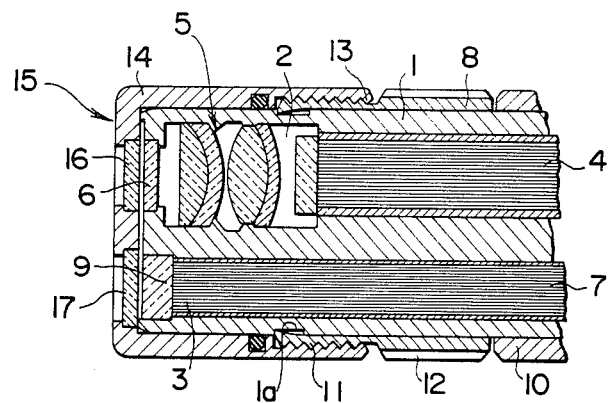
FIG. 8 is a section view of essential parts of the distal end of an endoscope according to a third embodiment of the present invention.
Figure 9:
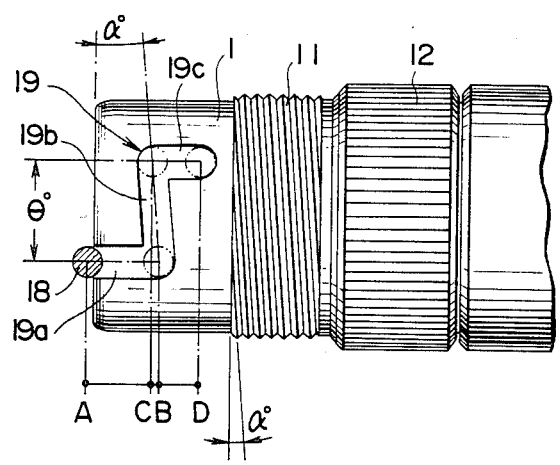
FIG. 9 is a side view of essential parts of the distal end of the endoscope shown in FIG. 8 from which a cap is removed.

A third embodiment of the present invention shown in FIGS. 8 and 9 differs from the first embodiment in that the peripheral groove 19b of the fitting groove 19 provided on the distal end member 1 is formed to have the same angle of inclination $\alpha°$ as the lead angle $\alpha°$ of the female thread 13 provided on the cap 14 without dividing the female thread 13 into two. Accordingly, like elements are given the same reference characters as those of the first embodiment.

In the third embodiment, when the cap 14 is completely coupled to the cap screw body 8, the pin 18 is located at the terminal end of the axial groove 19c and the observation and illumination windows 16, 17 are respectively in alignment with the cover glass 16 of the observation optical system 2 and the cover glass 9 of the illumination optical system 3.

In operation, the cap 14 is fitted into the distal end member 1 of the endoscope to fit the pin 18 into the fitting groove 19. At this time, the pin 18 is at a position A in FIG. 9. Subsequently, the cap screw body 8 is rotated while the female thread 13 of the cap 14 threadably engages with the male thread 11 of the cap screw body 8. With the rotation, the cap 14 is drawn in while the pin 18 moves within the axial groove 19a, so that the pin 18 reaches a position B adjacent to the rear of the axial groove 19a. Since the position B is where part of the pin 18 is in contact with the side wall of the fitting groove 19, the cap 14 cannot be further drawn in.

Now, when the cap 14 or the pin 18 is rotated, the pin 18 is moved in the axial direction through a lead angle $\alpha°$ and thereby rotates through the angle $\alpha°$ along the peripheral groove 19b having an angle of inclination $\theta°$ to stop against the side wall (a position C) of the axial groove 19c. Then, when the cap screw body 8 is further rotated, the cap 14 or the pin 18 is drawn in along the axial groove 19c. When the inner bottom surface of the cap 14 abuts against the front end surface of the distal end member 1 at a position D, the mounting operation of the cap 14 is completed. It will be understood that when the cap 14 is removed the foregoing operations are reversed.

In the third embodiment, since the peripheral grooves 19b formed on the distal end member 1 has the same angle of inclination $\alpha°$ as the lead angle $\alpha°$ of the male and female threads 11, 13, the pin 18 is not brought into contact with the side wall of the peripheral groove 19b even when the cap 14 is rotated. Consequently, no binding is caused between the male and female threads 11, 13 and thus the cap 14 is easily removably mounted.

In addition, since the peripheral groove 19b has an angle of inclination, it is possible to reduce the axial lengths of the groove and hence the distal end member 1 as a whole.

While the foregoing embodiments are described using right-handed thread in the threading means, the present invention is applicable to the case using left-handed thread. Accordingly, the peripheral groove 19b in the third embodiment may be inclined in accordance with the lead angle of left-handed thread.

Furthermore, it may be possible to increase the lead angle by using a multiple-thread screw, so that the overall length of the distal end member can be reduced.

It may also be possible to provide the pin in the distal end of endoscopes and the fitting groove on the inner peripheral surface of the cap.

What is claimed is:

1. An endoscope comprising:
   a distal end member thereof;
   a cap screw body rotatably disposed on said distal end member and having male threading means for mounting a cap;
   a cap adapted to be detachably fitted onto said distal end member and having female threading means for threadably engaging with said male threading means of said cap screw body and a pin projectingly provided therein;
   fitting groove means provided on the outer peripheral surface of said distal end member for fitting said pin, said fitting groove means including an axial groove and a peripheral groove; and
   cap mounting facilitating means for facilitating operation which detachably mounts said cap onto said distal end member eliminating binding between said male and female threading means of said cap screw body and said cap which would be caused by pushing said pin against the side wall of said peripheral groove by engagement between said male and female threading means while said pin moves within said peripheral groove;
   said cap mounting facilitating means releasing engagement between said male and female threading means of said cap screw body and said cap while said pin moves within said peripheral groove.

2. An endoscope according to claim 1 in which said male and female threading means includes a male thread provided on said cap screw body and two female threads of the same diameter dividedly provided on said cap in slightly wider space than the axial length of said male thread, respectively.

3. An endoscope according to claim 1 in which said male and female threading means includes a female thread provided on said cap and two male threads of the same diameter dividedly provided on said cap screw body in slightly wider space than the axial length of said female thread, respectively.

4. An endoscope comprising:
   a distal end member thereof;
   a cap screw body rotatably disposed on said distal end member and having male threading means for mounting a cap;
   a cap adapted to be detachably fitted onto said distal end member and having female threading means for threadably engaging with said male threading means of said cap screw body and a pin projectingly provided therein;
   fitting groove means provided on the outer peripheral surface of said distal end member for fitting said pin, said fitting groove means including an axial groove and a peripheral groove; and
   cap mounting facilitating means for facilitating operation which detachably mounts said cap onto said distal end member eliminating binding between said male and female threading means of said cap screw body and said cap which would be caused by pushing said pin against the side wall of said peripheral groove by engagement between said male and female threading means while said pin moves within said peripheral groove;

said male and female threading means including a male thread provided on said cap screw body and two female threads of the same diameter dividedly provided on said cap in slightly wider space than the axial length of said male thread, respectively.

5. An endoscope comprising:

a distal end member thereof;

a cap screw body rotatably disposed on said distal end member and having male threading means for mounting a cap;

a cap adapted to be detachably fitted onto said distal end member and having female threading means for threadably engaging with said male threading means of said cap screw body and a pin projectingly provided therein;

fitting groove means provided on the outer peripheral surface of said distal end member for fitting said pin, said fitting groove means including an axial groove and a peripheral groove; and cap mounting facilitating means for facilitating operation which detachably mounts said cap onto said distal end member eliminating binding between said male and female threading means of said cap screw body and said cap which wound be caused by pushing said pin against the side wall of said peripheral groove by engagement between said male and female threading means while said pin moves within said peripheral groove;

said male and female threading means including a female thread provided on said cap and two male threads of the same diameter dividedly provided on said cap screw body in slightly wider space than the axial length of said female thread, respectively.

6. An endoscope comprising:

a distal end member thereof;

a cap screw body rotatably disposed on said distal end member and having male threading means for mounting a cap;

a cap adapted to be detachably fitted onto said distal end member and having female threading means for threadably engaging with said male threading means of said cap screw body and a pin projectingly provided therein;

fitting groove means provided on the outer peripheral surface of said distal end member for fitting said pin, said fitting groove means including an axial groove and a peripheral groove; and cap mounting facilitating means for facilitating operation which detachably mounts said cap onto said distal end member eliminating binding between said male and female threading means of said cap screw body and said cap which would be caused by pushing said pin against the side wall of said peripheral groove by engagement between said male and female threading means while said pin moves within said peripheral groove;

said cap mounting facilitating means is constituted by said peripheral groove which has an inclination of the same angle as the lead angle of said threading means.

7. An endoscope according to claim 6 in which said threading means employs a multiple-thread screw.

8. An endoscope comprising:

a distal end member thereof;

a cap screw body rotatably disposed on said distal end member and having male threading means for mounting a cap;

a cap adapted to be detachably fitted onto said distal end member and having female threading means for threadably engaging with said male threading means of said cap screw body and a pin projectingly provided therein;

fitting groove means provided on the outer peripheral surface of said distal end member for fitting said pin, said fitting groove means including an axial groove and a peripheral groove; and cap mounting facilitating means for facilitating operation which detachably mounts said cap onto said distal end member eliminating binding between said male and female threading means of said cap screw body and said cap which would be caused by pushing said pin against the side wall of said peripheral groove by engagement between said male and female threading means while said pin moves within said peripheral groove;

said threading means employing a multiple-thread screw.

* * * * *